United States Patent

Pandl et al.

[11] Patent Number: 5,206,426
[45] Date of Patent: Apr. 27, 1993

[54] PHENYLENE DIAMINES AND PROCESS FOR THE PREPARATION OF PHENYLENE DIAMINES

[75] Inventors: Klaus Pandl, Ludwigshafen; Manfred Patsch, Wachenheim, both of Fed. Rep. of Germany

[73] Assignee: BASF Aktiengesellschaft, Ludwigshafen, Fed. Rep. of Germany

[21] Appl. No.: 815,159

[22] Filed: Dec. 31, 1991

Related U.S. Application Data

[62] Division of Ser. No. 509,137, Apr. 16, 1990, Pat. No. 5,117,050.

[30] Foreign Application Priority Data

May 3, 1989 [DE] Fed. Rep. of Germany ....... 3914650

[51] Int. Cl.$^5$ ............................................. C07C 309/29
[52] U.S. Cl. ........................................ 562/52; 562/55
[58] Field of Search ...................... 562/47, 52, 55, 58

[56] References Cited

U.S. PATENT DOCUMENTS 4,973,671 11/1990 Pandl et al. .................... 534/618

*Primary Examiner*—Nicky Chan
*Attorney, Agent, or Firm*—Oblon, Spivak, McClelland, Maier & Neustadt

[57] ABSTRACT

Phenylene diamines of the formula

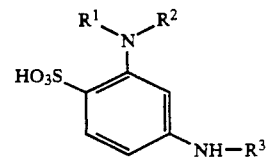

in which
$R^1$ denotes hydrogen, formyl or oxalyl,
$R^2$ denotes hydrogen or $C_1$-$C_4$-alkyl and
$R^3$ denotes hydrogen or $C_2$-$C_8$-alkanoyl, provided that $R^1$ and $R^2$ are not both hydrogen and that when $R^2$ is methyl or ethyl, $R^1$ and $R^3$ are not both hydrogen, and a process for the preparation of phenylene diamines.

1 Claim, No Drawings

PHENYLENE DIAMINES AND PROCESS FOR THE PREPARATION OF PHENYLENE DIAMINES

This is a division, of application Ser. No. 07/509,137, filed on Apr. 16, 1990, now U.S. Pat. No. 5,117,050.

The present invention relates to phenylene diamines of formula I

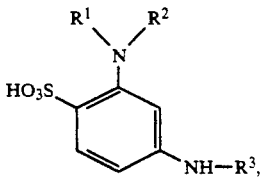

in which $R^1$ denotes hydrogen, formyl or oxalyl, $R^2$ denotes hydrogen or $C_1$–$C_4$-alkyl and $R^3$ denotes hydrogen or $C_2$–$C_8$-alkanoyl, provided that $R^1$ and $R^2$ are not both hydrogen and that when $R^2$ is methyl or ethyl, $R^1$ and $R^3$ are not both hydrogen, and to a process for the preparation of phenylene diamines.

Prior patent application EP-A 315,045 discloses 4-amino-2-(N-methylamino)benzenesulfonic acid and 4-amino-2-(N-ethylamino)benzenesulfonic acid.

It is an object of the present invention to provide novel phenylene diamines and a process for the preparation thereof.

Accordingly, we have found the phenylene diamines of formula I defined above.

All of the alkyl groups occurring in the above formula I may be linear or branched.

$R^2$ denotes, for example, methyl, ethyl, propyl, isopropyl, butyl, isobutyl or s-butyl.

$R^3$ denotes, for example, acetyl, propionyl, butyryl, isobutyryl, pentanoyl, hexanoyl, heptanoyl, octanoyl or 2-ethylhexanoyl.

We have further found that a phenylene diamine of formula I.

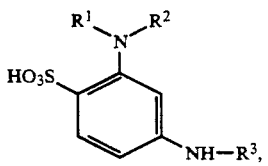

in which $R^1$ stands for hydrogen, formyl or oxalyl, $R^2$ stands for hydrogen or $C_1$–$C_4$-alkyl and $R^3$ stands for hydrogen or $C_2$–$C_8$-alkanoyl, provided that $R^1$ and $R^2$ are not both hydrogen, is advantageously prepared by treating 1,3-diaminobenzene-4-sulfonic acid first with formic or oxalic acid and then, if desired, with an acylating agent derived from a $C_2$–$C_8$-alkanoic acid, and in a second stage, if desired, reacting the resulting acyl-derivative of formula II

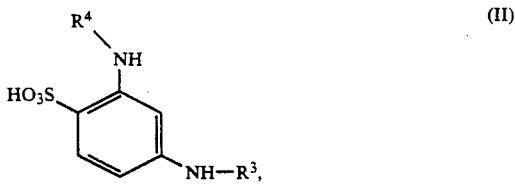

in which $R^4$ denotes formyl or oxalyl and $R^3$ has the meaning stated above, with an alkylating agent of formula III

$$R^5\text{—}X, \quad (III)$$

in which $R^5$ is $C_1$–$C_4$-alkyl and X is a leaving group, and in a third stage, if desired, hydrolytically removing the formyl or oxalyl group and, if desired, the $C_2$–$C_8$-alkanoyl radical.

The process of the invention is conveniently carried out by treating 1,3-diaminobenzene-4-sulfonic acid with formic or oxalic acid, in aqueous solution, at a temperature of from 90° to 100° C., the concentration of acid in the aqueous solution generally being from 5 to 98% w/w and preferably from 5 to 30% w/w, based on the weight of the solution. In general, for each mole of diaminobenzene there will be used from 1.2 to 4.0 mole equivalents of acid. The use of formic acid is preferred.

Following a reaction time of, usually, from 0.5 to 5 hours and preferably from 1.5 to 3 hours, the resulting 3-(N-formylamino)aniline-4-sulfonic acid or 3-(N-oxalylamino)aniline-4-sulfonic acid is precipitated at a pH of from 1 to 7, preferably from 1 to 3.5 or from 5 to 7, if necessary with the addition of sodium chloride, and then isolated by filtration in vacuo. Alternatively, the reaction solution may be further processed as it is.

Following the treatment with formic or oxalic acid, treatment with an acylating agent derived from a $C_2$–$C_8$-alkanoic acid may be carried out. Such treatment is usually effected in an aqueous reaction medium.

The acylating agent used is usually the corresponding carboxylic anhydride or a mixture of carboxylic anhydrides, or the corresponding carboxyl halide. Examples are acetic anhydride, propionic anhydride, acetyl chloride and propionyl chloride. We prefer to use propionic anhydride and. more preferably, acetic anhydride.

For each mole of phenylene diamine there will usually be used from 1.1 to 2.0 moles and preferably from 1.1 to 1.7 moles of acylating agent. The acylation is generally carried out at a temperature of from 10° to 45° C., preferably from 20° to 30° C., and at a pH of from 3 to 7.5, preferably from 5.5 to 6.5.

On completion of the reaction, which generally takes from 15 to 90, preferably from 30 to 60, minutes, the acylation product of formula II ($R^3 = C_2$–$C_8$-alkanoyl) can be precipitated with sodium chloride at a pH of from 0.5 to 7.5, preferably from 3 to 4.5. Alternatively, the resulting reaction solution may be further processed as it is.

In a preferred embodiment, the process is carried out without using an acylating agent, i.e. alkylation follows directly on the treatment with formic or oxalic acid. Also, we prefer to do this without isolating the reaction product. Before alkylation commences, the pH of the aqueous solution is adjusted to 6-7.

Those compounds of formula I in which $R^2$ stands for $C_1$–$C_4$-alkyl may be obtained, for example, by reacting the acylation product II with an alkylating agent III $R^5-X$ (III), in which $R^5$ stands for $C_1-C_4$-alkyl and X stands for a leaving group.

A suitable leaving group X is, for example, halogen such as chlorine, bromine and iodine, or a radical of the formula $O-SO_2-C_6H_5$, $O-SO_2-C_6H_4-CH_3$ or $O-SO_2-OR^5$, in which $R^5$ has the meaning stated above. The use of $C_1-C_4$-dialkyl sulfates, in particular dimethyl sulfate, is preferred.

The alkylation reaction is carried out by known methods in an aqueous reaction medium in the presence of a base such as sodium or potassium hydroxide, sodium hydroxide being preferred. For each mole of acylation product II there will generally be used from 1.0 to 2.0, preferably from 1.2 to 1.7, moles of alkylating agent III. For each mole equivalent of alkylating agent III there will normally be used from 1 to 2, preferably from 1.1 to 1.3, moles of base.

The reaction temperature is usually from 10° to 80° C. When working with dimethyl sulfate, it is preferred to use a temperature of from 10° to 50° C., in particular from 20° to 35° C., whilst temperatures ranging from 40° to 80° C. are to be preferred when working with diethyl sulfate.

The order in which the reactants are added is arbitrary. The reaction is generally complete after running for 5 to 30 minutes, and the reaction product can then be isolated by known methods.

However, the hydrolytic removal of the formyl or oxalyl group and of the $C_2-C_8$-alkanoyl radical may, if desired, be effected directly, i.e. without isolating the product. This may be carried out in an acidic or an alkaline medium.

When operating in an acid medium, the acidifying agent used may be, for example, hydrochloric or sulfuric acid giving a pH of from −0.5 to +2, preferably from −0.5 to +0.5. When operating in alkaline medium, the basifying agent used is, for example, from 1 to 6 moles of sodium or potassium hydroxide per mole of the product to be deacylated.

Under both acidic and alkaline conditions, hydrolytic cleavage is effected by heating under reflux. Cleavage is complete after a reaction time of from 2 to 3 hours, and the target product can be isolated by known methods.

Our novel process, which can be carried out batchwise or continuously, produces the phenylene diamines I of the invention in a simple manner. These products are valuable intermediates for the synthesis of dyes, for example reactive dyes, such as are described in the prior patent application EP-A 315,045.

The invention is illustrated below with reference to Examples.

EXAMPLE 1

94 g of 1,3-diaminobenzene-4-sulfonic acid in 430 ml of water and 70 g of formic acid were boiled for 3 hours under reflux. The mixture was cooled to 20° C., and the resulting 3-(N-formylamino)aniline-4-sulfonic acid was filtered off in vacuo and stirred in 500 g of water with the addition of caustic soda solution to give a pH of 6.5. 70 g of acetic anhydride were then added and the pH was kept between 5.0 and 6.5 by the addition of caustic soda solution. After 30 minutes, the pH was adjusted to 12.5 with caustic soda solution, and 75 g of dimethyl sulfate were added dropwise. After 30 minutes, the pH was adjusted to -0.5 with hydrochloric acid, and the mixture was boiled under reflux for 3 hours. After cooling, the mixture was adjusted to pH 1.0 with caustic soda solution and salted out with 150 g of sodium chloride. The precipitated 3-(N-methylamino)aniline-4-sulfonic acid was isolated by filtration in vacuo.

$^{13}C$-NMR data: 3-(N-formylamino)aniline-4-sulfonic acid δ ($d^6$-DMSO): 173.6 (d), 153.3 (s), 148.0 (s), 131.6 (d), 120.6 (s), 106.4 (d), 105.5 (d).

3-(N-methylamino)aniline-4-sulfonic acid, δ ($d^6$-DMSO): 153.8 (s), 150.5 (s), 131.8 (d), 120.2 (s), 106.2 (d), 100.8 (d), 32.5 (q).

EXAMPLE 2

115 g of 3-(N-acetylamino)aniline-4-sulfonic acid in 430 ml of water and 70 g of formic acid were boiled under reflux for 7 hours. The mixture was cooled to 20° C. and its pH then adjusted to 12 with caustic soda solution. 75 g of dimethyl sulfate were then added, and after 40 minutes the pH was adjusted to -0.5 with hydrochloric acid. The mixture was heated under reflux for 3 hours and then salted out with 150 g of sodium chloride. The pH was adjusted to 1.0 with caustic soda solution, and the precipitated 3-(N-methylamino)aniline-4-sulfonic acid was isolated by filtration.

EXAMPLE 3

94 g of 1,3-diaminobenzene-4-sulfonic acid in 430 ml of water and 70 g of formic acid were boiled under reflux for 3 hours. Then, at 20° C., 100 ml of water were added and the pH was adjusted to 6.5 with caustic soda solution. 70 g of acetic anhydride were then added, the pH being kept between 5.5 and 6.5 with caustic soda solution. The pH was then adjusted to 12.5 with caustic soda solution, and 75 g of dimethyl sulfate were added. After 30 minutes, 110 g of 50% w/w caustic soda solution were added, and the mixture was boiled under reflux at 100° C. for 3 hours. 150 ml of water were then distilled off and the pH was adjusted to 1 with hydrochloric acid. At 20° C., the precipitated 3-(N-methylamino)aniline-4-sulfonic acid was isolated by filtration.

EXAMPLE 4

47 g of 1,3-diaminobenzene-4-sulfonic acid in 215 ml of water and 35 g of formic acid were heated under reflux for 3 hours. The pH was then adjusted to 6.5 with caustic soda solution and, at 20° C., 35 g of acetic anhydride were added dropwise, while the pH was kept between 6.0 and 7.0 with caustic soda solution. After 1 hour, the pH was adjusted to 4.0 with hydrochloric acid, and 200 g of sodium chloride were added. Stirring was continued for 5 hours, after which the precipitated 1-(N-acetylamino)-3-(N-formylamino)benzene-4-sulfonic acid was isolated by filtration.

$^{13}C$-NMR data: 1-(N-acetylamino)-3-(N-formylamino)benzene-4-sulfonic acid δ ($d^6$-DMSO): 168.8 (s), 159.9 (d), 140.5 (s), 134.4 (s), 130.0 (s), 127.7 (d), 113.7 (d), 111.5 (d), 23.8 (q).

EXAMPLE 5

220 g of 3-(N-formylamino)aniline-4-sulfonic acid in 1,500 ml of water were reacted with 140 g of acetic anhydride at a pH of 5.0 to 5.5. The mixture was heated, at pH 7.0, to 50° C., and 200 g of diethyl sulfate were added. The pH was then adjusted to 12.5 to 13.0 with caustic soda solution and stirring was continued for 2 hours. The pH was then adjusted to -0.5 to 0 with hydrochloric acid, and the mixture was boiled under reflux at 100° C. for 3 hours. After cooling, it was adjusted to pH 1.0 with caustic soda solution, and 200 g of sodium chloride were added. The precipitated 3-(N-ethylamino)aniline-4-sulfonic acid was then isolated by filtration in vacuo.

$^{13}$C-NMR data: 3-(N-ethylamino)aniline-4-sulfonic acid δ (d$^6$-DMSO): 142.7 (s), 137.7 (s), 128.6 (s and d), 109.1 (d), 104.8 (d), 34.4 (t), 13.5 (q).

EXAMPLE 6

Example 4 was repeated except that 42 g of propionic anhydride were used instead of acetic anhydride. The product obtained was 1-(N-propionylamino)-3-(N-formylamino)benzene-4-sulfonic acid.

$^{13}$C-NMR data: δ (d$^6$-DMSO): 172.2 (s), 159.7 (d), 140.4 (s), 134.4 (s), 130.1 (s), 127.5 (d), 113.4 (d), 111.1 (d), 29.5 (t), 9.4 (q).

EXAMPLE 7

Example 1 was repeated except that 86 g of propionic anhydride were used instead of acetic anhydride. There was obtained 3-(N-methylamino)aniline-4-sulfonic acid.

EXAMPLE 8

97 g of 1,3-diaminobenzene-4-sulfonic acid were stirred with 250 ml of water and, after the addition of 38 ml of 98% w/w formic acid, boiled at 95°–100° C. The mixture was then colled to 30° C., and 65 g of ice were added, the pH being adjusted to 6.5 to 7.0 with 60.5 ml of 50% w/w caustic soda solution. There were then added 45 ml of 50% w/w caustic soda solution and 70 ml of dimethyl sulfate, and stirring was continued for 30 minutes. The mixture was then acidified with 43 ml of 96% w/w sulfuric acid and stirred at 100° C. for 3 hours. The mixture was then cooled, and the precipitated 3-(N-methylamino)aniline-4-sulfonic acid was isolated by filtration.

We claim:
1. A phenylene diamine of formula I

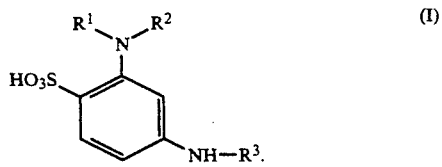

in which
R$^1$ denotes formyl or oxalyl,
R$^2$ denotes hydrogen or C$_1$–C$_4$-alkyl and
R$^3$ denotes C$_2$–C$_4$-alkanoyl.

* * * * *